United States Patent
Mukai et al.

(10) Patent No.: US 7,138,143 B1
(45) Date of Patent: Nov. 21, 2006

(54) COATED PREPARATION SOLUBLE IN THE LOWER DIGESTIVE TRACT

(75) Inventors: Tadashi Mukai, Naruto (JP); Daisuke Kuribayashi, Kakogawa (JP)

(73) Assignee: Otsuka Pharmaceutical Company, Limited, Tokyo-to (JP)

(*) Notice: Subject to any disclaimer, the term of this patent is extended or adjusted under 35 U.S.C. 154(b) by 482 days.

(21) Appl. No.: 10/089,442

(22) PCT Filed: Sep. 22, 2000

(86) PCT No.: PCT/JP00/06496

§ 371 (c)(1),
(2), (4) Date: Mar. 29, 2002

(87) PCT Pub. No.: WO01/23000

PCT Pub. Date: Apr. 5, 2001

(30) Foreign Application Priority Data

Sep. 30, 1999 (JP) .................................. 11-279147
Mar. 17, 2000 (JP) .............................. 2000-076276

(51) Int. Cl.
A61K 9/16 (2006.01)
A61K 9/14 (2006.01)
A61K 9/50 (2006.01)

(52) U.S. Cl. ................. 424/490; 424/489; 424/497

(58) Field of Classification Search ........... 424/490, 424/489, 497
See application file for complete search history.

(56) References Cited

U.S. PATENT DOCUMENTS

| | | | |
|---|---|---|---|
| 4,385,078 A | 5/1983 | Onda et al. ............ | 427/3 |
| 5,026,559 A | 6/1991 | Eichel et al. ........... | 424/458 |
| 5,914,132 A | 6/1999 | Kelm et al. ............ | 424/478 |

FOREIGN PATENT DOCUMENTS

| | | |
|---|---|---|
| EP | 0 391 518 A2 * | 10/1990 |
| EP | 0 648 487 A1 * | 4/1995 |
| GB | 1 393 374 | 5/1975 |

OTHER PUBLICATIONS

"Organic acids as excipients in matrix granules for colon-specific drug delivery," P. Nykänen et al., International Journal of Pharmaceutics, 184 (1999) 251-261.

* cited by examiner

Primary Examiner—Humera N. Sheikh
(74) Attorney, Agent, or Firm—Finnegan, Henderson, Farabow, Garrett & Dunner, L.L.P.

(57) ABSTRACT

A coating dispersion soluble in the lower digestive tract which is prepared by blending a hydroxypropyl methylcellulose acetate succinate (HPMCAS) soluble at around pH 7 with a conventional plasticizer and an anion surfactant and further adding an acid, wherein the HPMCAS has an average particle size of 10 μm or less and is dispersed at a concentration of 2 to 20% by weight, and the acid is used in an amount of 1 to 10 parts by weight per 100 parts by weight of HPMCAS, and a sustained release coated preparation capable of releasing a medicament in the large intestine at the lower digestive tract, which is prepared by coating a medicament-containing solid preparation such as a granular core with the coating dispersion.

8 Claims, 1 Drawing Sheet

COATED PREPARATION SOLUBLE IN THE LOWER DIGESTIVE TRACT

TECHNICAL FIELD

The present invention relates to a coated preparation soluble in the lower digestive tract which can promote release of a medicament at the lower digestive tract, more particularly to a coating base dispersion suitable for preparing a coated preparation soluble in the lower digestive tract by coating the surface of a medicament-containing core granule, etc., and further to a coated granule for delivery to the large intestine which is prepared by coating a medicament-containing core granule with the coating dispersion soluble in the lower digestive tract.

BACKGROUND ART

Recently, many studies have been done for the development of sustained release preparations with enteric coating base materials. However, when these known preparations are administered, the medicament contained therein is mostly released during passing the small intestine. In some kinds of medicaments, it is desired to be prepared in a sustained release preparation which can also release the medicament in the large intestine as well as in the small intestine and thereby can exhibit the medical activity for a long period. However, when a pharmaceutical preparation is orally administered, it passes through various pH range regions until reaching to the large intestine, that is, from the stomach which is a strong acidic region to the small intestine which is a neutral or alkaline region. Accordingly, it is a great task to find a pharmaceutical preparation which can reach to the large intestine of the lower digestive tract after passing through the digestive tract having variable pH ranges. Particularly, in order to prepare a pharmaceutical preparation which can release the active ingredient in the large intestine by administration once a day or to prepare a large intestine delivery preparation, it is required to keep the medicament without dissolution of the coating base material during passing through the ileum where the pH value raises to about 7.

Besides, when a pharmaceutical preparation is administered orally, it will usually take about 4 to 6 hours until reaching to the large intestine, and in case of a sustained release preparation which is formulated so as to administer once a day, it shall gradually release the medicament even after reached to the large intestine. Otherwise, a sufficiently high blood concentration of the medicament can not be maintained for 24 hours and hence the desired therapeutic effects can not be obtained. In other words, such a pharmaceutical preparation shall satisfy the requirements that it surely reaches to the large intestine and releases a sufficient amount of the medicament in the large intestine.

The conventional enteric coating base materials are mostly dissolve at a pH range lower than 7, and the enteric coating base materials soluble at around pH 7 are an acrylic coating material such as methacrylic acid-methyl methacrylate copolymer (Eudragit S, manufactured by Roehm) and a cellulosic coating material (e.g. hydroxypropyl methylcellulose acetate succinate (AQOAT AS-HF, manufactured by Shin-Etsu Chemical Co., Ltd.). These enteric coating materials are used for the coating in the form of a solution in an organic solvent or in the form of an aqueous dispersion. In view of the recent environmental restriction, an organic solvent is limited to use and hence it tends to use an aqueous coating material (e.g. an aqueous dispersion).

JP-60-43334 discloses an acrylic coating emulsion as a coating material, but when such an acrylic coating emulsion is used, the enteric coating film is contaminated with a polymerization initiator, a chain transfer agent, unreacted monomers, etc., which are not suitable for medication in view of safety.

JP-56-12614 discloses an aqueous dispersion comprising a cellulosic coating material having an average particle size of 100 μm or less and a plasticizer. Such an aqueous dispersion has less stability to heat and has defects that the coating base material aggregates and then precipitates.

JP-7-109219 discloses an enteric coating dispersion comprising an enteric coating material having an average particle size of 10 μm or less, a plasticizer and an anionic surfactant, which is stably dispersed for a long period without aggregation even by change of temperature. However, the hydroxypropyl methylcellulose acetate succinate (HPMCAS) used therein has a dissolving pH value of about 7 even at a grade of the highest dissolving pH value and it dissolves in a wide range of pH values. Accordingly, when a pharmaceutical preparation coated with such a coating material is administered orally, it dissolves in a small intestine and releases the medicament mostly in the small intestine.

JP-2-289512 discloses a pharmaceutical preparation comprising an enteric coated core granule and a large amount of an organic acid (30 to 50% by weight based on the weight of the core granules) so as to give an alkaline resistance even at a raised pH value. However, it is reported by Nykanen et al. (International Journal of Pharmaceutics, vol. 184, pp. 251–261, 1999) that even when a large amount of an acid is added to the core granule in an enteric coated granule preparation coated with HPMCAS, said preparation could not show the desired sustained release of the medicament (ibuprofen) in vivo test, and the blood level profile of the ibuprofen was similar to that in a granule to which no acid was added.

DISCLOSURE OF INVENTION

An object of the present invention is to provide a coated preparation for oral administration which can release the medicament even in the lower digestive tract, i.e. in the large intestine when administered orally, and to provide a coating dispersion soluble in the lower digestive tract suitable for achieving such a purpose, said coating base material used therein being not immediately dissolved during passing the ileum where the pH value raises to about 7.

The present invention provides also a large intestine delivery coated granule preparation which can sufficiently release the medicament in the large intestine and even after reached thereto, said preparation being prepared by coating a medicament-containing core granule with said coating dispersion soluble in the lower digestive tract. That is, the present invention provides a coating dispersion soluble in the lower digestive tract which is prepared by blending a hydroxypropyl methyl-cellulose acetate succinate (HPMCAS) soluble at around pH 7 with a conventional plasticizer and an anion surfactant and further adding an acid, wherein HPMCAS has an average particle size of 10 μm or less and is dispersed in a concentration of 2 to 20% by weight, and the acid is incorporated in an amount of 1 to 10 parts by weight per 100 parts by weight of HPMCAS. The present invention provides also a large intestine delivery coated granule preparation being able to release a medicament even in the large intestine region which is prepared by coating a medicament-containing core granule with said coating dispersion soluble in the lower digestive tract.

BRIEF DESCRIPTION OF DRAWING

FIG. 2 is a graph showing a dissolution behavior of the medicament at pH 6.5 of the coated granules prepared in Example 12 of the present invention and of the coated granule of Reference Example 3.

BEST MODE FOR CARRYING OUT THE INVENTION

Figure 1:
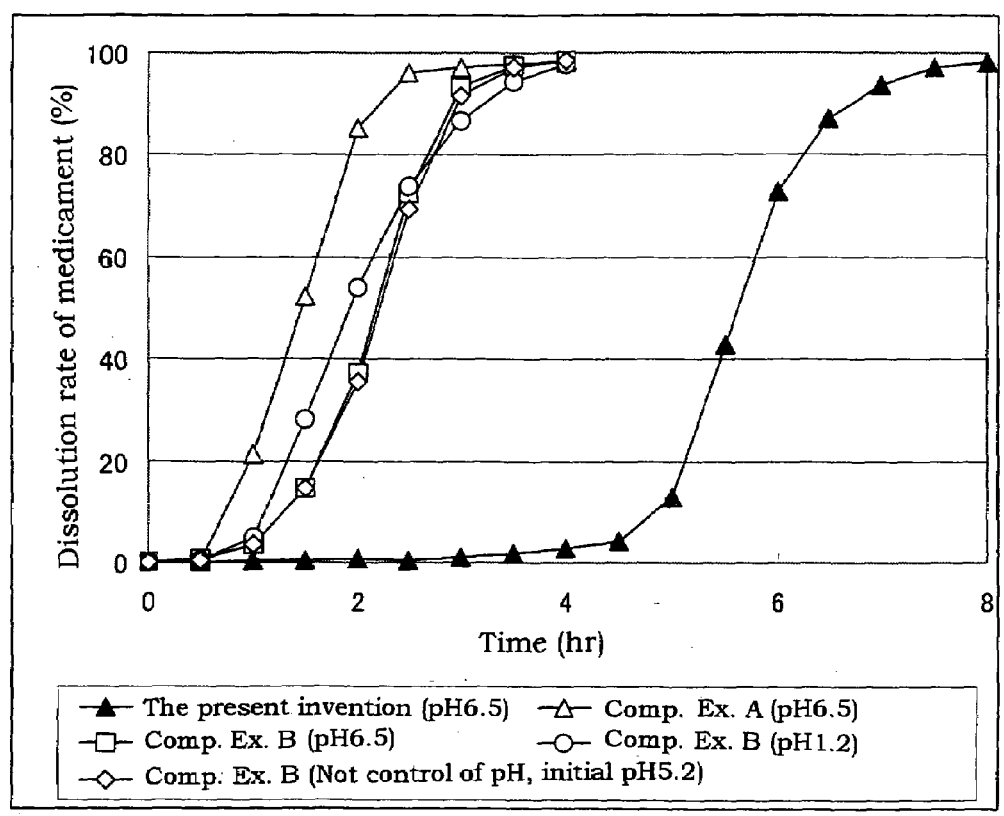
FIG. 1 is a graph showing a dissolution behavior of the medicament at pH 6.5 of the coated granules prepared in Examples 3 to 8 which are a coated preparation soluble in the lower digestive tract of the present invention and of the coated granules of Reference Examples 1 to 2.

The HPMCAS soluble at around pH 7 includes, for example, a commercially available AQOAT AS-HF (manufactured by Shin-Etsu Chemical Co., Ltd.) but should not be limited thereto.

The acid includes, for example, organic acids, such as citric acid, ascorbic acid, adipic acid, ethylenediaminetetraacetic acid, lactic acid, succinic acid, etc., phosphoric acid, a high molecular acid, and an acidic iron exchange resin. These may be used alone or in a combination of two or more thereof. Preferred acid is an organic acid, particularly citric acid.

The plasticizer includes, for example, triethyl citrate or triacetyl. These may be used alone or in a combination of two or more. Preferred one is triethyl citrate.

The anion surfactant includes, for example, sodium alkylsulfate (e.g. sodium laurylsulfate, dioctyl sodium sulfosuccinate, etc.), fatty acid sodium salt (e.g. sodium oleate, etc.), and fatty acid potassium salt (e.g. potassium sorbate, etc.). These may be used alone or in a combination of two or more thereof. Preferred one is sodium alkylsulfates, particularly sodium laurylsulfate.

For coating of granules, it is effective to add talc and the like in order to prevent aggregation of the granules during coating procedure.

The coating dispersion soluble in the lower digestive tract of the present invention is easily prepared by adding an acid to the coating dispersion prepared by a conventional method.

HPMCAS soluble at around pH 7 is used in an amount of 2 to 20% by weight, preferably 5 to 15% by weight, based on the whole weight of the coating dispersion soluble in the lower digestive tract. When HPMCAS is used in a concentration lower than the above range, the coating procedure takes undesirably a longer time, and on the other hand, when its concentration is higher than the above range, the coating base material undesirably aggregates with raising of temperature during storage of the coating preparation or during coating procedure.

The acid is added in an amount of 1 to 10 parts by weight, preferably 2 to 5 parts by weight, per 100 parts by weight of HPMCAS. When the acid is used in an amount less than the above, the coating layer of the preparation will dissolve before reaching to the lower digestive tract when administered, which results in insufficient release of the medicament in the large intestine, that is, it results in less extension of lag time. On the other hand, when the acid is added in too much amount, the coating base material easily aggregates, which undesirably causes unstable coating film.

The plasticizer is incorporated in an amount of 10 to 50 parts by weight, preferably 30 to 50 parts by weight, per 100 parts by weight of HPMCAS.

The anion surfactant is incorporated in an amount of 0.5 to 10 parts by weight, preferably 1 to 5 parts by weight, per 100 parts by weight of HPMCAS.

The coating dispersion soluble in the lower digestive tract of the present invention may optionally be incorporated by an aggregation inhibitor (e.g. talc), a colorant (e.g. pigment), a flavoring substance (e.g. thaumatin), and the like.

The large intestine delivery coated granule preparation of the present invention may be prepared by coating a medicament-containing core granule with the coating dispersion soluble in the lower digestive tract according to a conventional coating method.

The coating is usually carried out by spraying the above coating dispersion soluble in the lower digestive tract onto medicament-containing core granules and treating the sprayed granules with a coating apparatus in a usual manner. The spray of the dispersion onto the medicament-containing core granules is carried out by any spray apparatus such as an air spray apparatus or an airless spray apparatus. When there is a possibility that a solid material (i.e. pigment) deposits, the spraying may preferably be done with stirring the dispersion. The coating machine may be, for example, a pan coating machine, a drum type coating machine, a fluidized bed coating machine, or a fluid agitating coating machine.

The coating dispersion soluble in the lower digestive tract may be used in such an amount that the coating thickness is in the range of 30 to 150 µm, preferably 50 to 150 µm. When the coating amount is converted to the amount of HPMCAS soluble at around pH 7, it is in the range of 20 to 200 parts by weight, preferably 30 to 100 parts by weight, per 100 parts by weight of the medicament-containing granule.

The medicament-containing core granule is not limited with respect to the medicament and the pharmaceutically acceptable carrier. It may be a medicament alone, or it may contain an acid within the core granule.

The large intestine delivery coated granule preparation of the present invention is usually used as a pharmaceutical preparation in the form of granules, capsules, or tablets, and optionally it may be combined with granules or tablets having different dissolution rate of a medicament.

These pharmaceutical preparations may be prepared by a conventional method.

The coating dispersion soluble in the lower digestive tract of the present invention may also be used for forming a coating film soluble in the lower digestive tract onto other medicament-containing solid pharmaceutical preparation such as pills, tablets or capsules in addition to the above-mentioned medicament-containing core granule.

The coating dispersion soluble in the lower digestive tract and the large intestine delivery coated granule with said coating dispersion of the present invention are illustrated in more specifically by the following examples, but it should not be construed to be limited thereto.

EXAMPLE 1

Triethyl citrate (84 g, 2.8%), sodium laurylsulfate (6.3 g, 0.21%) and citric acid (6.3 g, 0.21%) are dissolved in a purified water (2588.4 g), and thereto are dispersed a hydroxypropyl methylcellulose acetate (the tradename: AQOAT AS-HF, manufactured by Shin-Etsu Chemical Co., Ltd.)(210 g, 7.0%) and talc (105 g, 3.5%) to give a coating dispersion.

Separately, cilostazol powder having an average particle size of about 2 μm (400 g) which is prepared by pulverized by a jet mill, a hydroxypropyl methylcellulose acetate succinate (a tradename: AQOAT AS-LF, manufactured by Shin-Etsu Chemical Co., Ltd.) (160 g), a hydroxypropyl methylcellulose (40 g) (as a binder), and sodium laurylsulfate (40 g) (as a dispersing agent and/or a solubilizer) are mixed in a kneader (NSK-150, manufactured by Okada Seiko K.K.) and the mixture is mixed with an appropriate amount of an aqueous solution of sodium chloride (20 g), citric acid (20 g) and polysorbate 80 (20 g) to obtain a kneaded mixture. Said wetted mixture is taken out and granulated with an extrusion granulator equipped with a dome die (0.8 mm hole) (Domegran DG-L1, manufactured by Fuji Powdal K.K.) and then formed in spherical shape with a spherical granulator (Malmerizer QJ-400, manufactured by Fuji Powdal K.K.). The granules thus obtained are dried, and the granules having a particle size of 710–1000 μm are collected to give core granules.

The core granules for coating (600 g) are entered into a fluid agitation coating machine (New Malmerizer NQ-160, manufactured by Fuji Powdal K.K.) and thereto is sprayed the coating dispersion prepared above (2570 g), and the resultant is dried to give coated granules. The coated granules of about 280 mg contain cilostazol of about 100 mg.

REFERENCE EXAMPLE 1

Separately, cilostazol powder having an average particle size of about 2 μm (100 g) which is prepared by pulverized by a jet mill, a hydroxypropyl methylcellulose (75 g), lactose (195 g) and mannitol (30 g) are mixed, and the mixture is granulated with adding purified water (110 g) and dried to give granules for tabletting for the outer layer. The granules for tabletting for the outer layer (400 mg) contain cilostazol (about 100 mg).

The coated granules obtained in Example 1 (about 280 mg), the above granules for tabletting for the outer layer (400 mg) and magnesium stearate (4 mg) are mixed, and then tabletted with a stamper and quern (diameter: 11 mm) to give sustained release tablets containing cilostazol of 200 mg/tablet.

EXAMPLE 2

Triethyl citrate (160 g), sodium laurylsulfate (12 g) and citric acid (13 g) are dissolved in a purified water (5215 g), and thereto are dispersed a hydroxypropyl methylcellulose acetate succinate (AQOAT AS-HF)(400 g) and talc (200 g) to give a coating dispersion.

Separately, cilostazol powder having an average particle size of about 2 μm (150 g) which is prepared by pulverized by a jet mill, a hydroxypropyl methylcellulose acetate succinate (AQOAT AS-LF, manufactured by Shin-Etsu Chemical Co., Ltd.) (60 g), a hydroxypropyl methylcellulose (Metrose 90SH400, manufactured by Shin-Etsu Chemical Co., Ltd.) (15 g) and sodium laurylsulfate (12.5 g) are mixed. The mixture is transferred into a kneader and thereto is added a mixture of sodium chloride, citric acid and polysorbate 80 (each 7.5 g) and thereto is further added purified water to obtain a kneaded mixture. The resulting mixture is granulated with an extrusion granulator equipped with a dome die (0.8 mm hole) and then formed in spherical shape with a spherical granulator. The same procedure is repeated six times and the granules thus obtained are dried, and the granules having a particle size of 710 μm –1000 μm are collected to give core granules. The core granules of 260 mg contain cilostazol of 150 mg.

The core granules for coating (1040 g) are entered into a fluid agitation coating machine and thereto is sprayed the coating dispersion prepared above (4800–5300 g) to give coated granules, in which the coating is terminated when the content of cilostazol is reached to 417 mg from 150 mg, and the resultant is dried with heating to give a sustained release coated granules.

REFERENCE EXAMPLE 2

Separately, cilostazol powder having an average particle size of about 2 μm (500 g) which is prepared by pulverized by a jet mill, a crystalline cellulose (100 g), corn starch (100 g), calcium carmelose (50 μg) and hydroxypropylcellulose (15 g) are mixed, and the mixture is granulated in a kneader with adding an appropriate amount of purified water (as a binder). After fluid-drying and sieving the granules, the sieved granules are mixed with magnesium stearate (5 g, as a lubricant) and then tabletted with a stamper and quern (diameter: 6.5 mm) to give immediate release tablets (one table: 77 mg corresponding to 50 mg of cilostazol).

The sustained release coated granules obtained in Example 2 (amount corresponding to cilostazol 150 mg) and the above immediate release tablets (one tablet corresponding to cilostzol 50 mg) are packed in a capsule to give a sustained release capsule.

EXAMPLES 3 TO 8 AND COMPARATIVE EXAMPLES 1 TO 2

Preparation of core granules for coating:

Using an extrusion granulator (Domegran DG-L1, manufactured by Fuji Powdal K.K.) equipped with a dome die (φ0.8 mm) granules are obtained from the kneaded products prepared with the formula as shown in Table 1 in the same manner as in Example 1, and the granules are formed in spherical shape with a spherical granulator (Malmerizer QJ-400, manufactured by Fuji Powdal K.K.) and dried, and then the granules having a particle size of 710 μm–1000 μm are collected by sieving to give core granules for coating.

TABLE 1

| Materials | Amounts |
| --- | --- |
| Cilostazol | 100 mg |
| Crystalline cellulose[*1] | 40 mg |
| Calcium carmelose[*2] | 40 mg |
| Sodium laurylsulfate[*3] | 10 mg |
| Hydroxypropylcellulose[*4] | 5 mg |
| Polysorbate 80[*5] | 5 mg |
| Totally | 200 mg |

[*1]Tradename, Avicel PH301 (manufactured by Asahi Kasei Corporation)
[*2]Tradename, ECG505 (manufactured by Gotoku Yakuhin K.K.)
[*3]Tradename, Nikkol SLS (manufactured by Nikko Chemicals K.K.)
[*4]Tradename, HPC-SL (manufactured by Nippon Soda Co. Ltd.)
[*5]Tradename, TO-10M (manufactured by Nikko Chemicals K.K.)

Besides, the same commercial products as above are used in the following examples.

Preparation of coating dispersions:

With the formula as shown in the following Table 2, coating dispersions soluble in the lower digestive tract are prepared in the same manner as described in Example 1 and Example 2.

TABLE 2

| Materials | Comp. Ex. 1 | Ex. 3–4 | Ex. 5–6 | Ex. 7–8 |
| --- | --- | --- | --- | --- |
| Hydroxypropyl methyl-cellulose acetate succinate | 7.00% | 7.00% | 7.00% | 7.00% |
| Triethyl citrate | 3.50% | 3.50% | 3.50% | 3.50% |
| Talc | 3.50% | 3.50% | 3.50% | 3.50% |
| sodium laurylsulfate | 0.07% | 0.07% | 0.07% | 0.07% |
| Citric acid | — | 0.07% | 0.21% | 0.35% |
| Purified water | 85.93% | 85.86% | 85.72% | 85.58% |
| Totally | 100.0% | 100.0% | 100.0% | 100.0% |

Preparation of coated granules:

Using the above-prepared core granules for coating and coating dispersions soluble in the lower digestive tract, the coated granule preparations are prepared each in the following manner.

The coating is carried out by using a fluid agitation coating machine (New Malmerizer NQ-160, manufactured by Fuji Powdal K. K.), and the granules are coated by spraying the coating dispersion using side spray under the conditions as shown in the following Table 3 so that the desired amount of HPMCAS is coated per the charged amount: 300 g of the core granule.

TABLE 3

| | | | |
| --- | --- | --- | --- |
| Supplied temperature | 70° C. | Exhaust temperature | 35–40° C. |
| Temp. of product | 30–35° C. | Air flow | 1.0 m³/min. |
| Feed rate of material | 10–20 g/min. | Revolution of coating plate | 100–300 rpm |

COMPARATIVE EXAMPLE 1

The above core granules are coated with the coating dispersion prepared with the formula of Comparative Example 1 in Table 2 in an amount of 53% by weight as HPMCAS to give coated granules.

COMPARATIVE EXAMPLE 2

In the same manner as described in Comparative Example 1 the above core granules are coated with the coating dispersion until the weight of HPMCAS becomes 75% by weight based on the weight of the core granules to give coated granules.

EXAMPLE 3

The core granules are coated with the coating dispersion prepared with the formula of Examples 3–4 in Table 2 under the conditions as mentioned above until the weight of HPMCAS becomes 40% by weight based on the weight of the core granules to give coated granules.

EXAMPLE 4

By using the same coating dispersion as used in Example 3 the core granules are coated under the above conditions until the weight of HPMCAS becomes 60% by weight based on the weight of the core granules to give coated granules.

EXAMPLE 5

The core granules are coated with the coating dispersion prepared with the formula of Examples 5–6 in Table 2 under the conditions as mentioned above until the weight of HPMCAS becomes 40% by weight based on the weight of the core granules to give coated granules.

EXAMPLE 6

By using the same coating dispersion as used in Example 4 the core granules are coated under the above conditions until the weight of HPMCAS becomes 60% by weight based on the weight of the core granules to give coated granules.

EXAMPLE 7

By using the coating dispersion prepared with the formula of Examples 7–8 in Table 2 under the conditions as mentioned above until the weight of HPMCAS becomes 40% by weight based on the weight of the core granules to give coated granules.

EXAMPLE 8

By using the same coating dispersion as used in Example 7 the core granules are coated under the above conditions until the weight of HPMCAS becomes 60% by weight based on the weight of the core granules to give coated granules.

EXAMPLES 9 To 11

Preparation of core granules for coating:

In accordance with the formula as shown in Table 4, the coated core granules are prepared in the same manner as described in Examples 3–8.

TABLE 4

| Materials | Example 9 | Example 10 | Example 11 |
| --- | --- | --- | --- |
| Cilostazol | 150.0 mg | 150 mg | 150 mg |
| Hydroxypropyl methyl-cellulose acetate succinate | 60.0 mg | 60 mg | 60 mg |
| Hydroxypropyl methyl-cellulose | 15.0 mg | 15 mg | 15 mg |
| Sodium laurylsulfate | 12.5 mg | 12.5 mg | 12.5 mg |
| Sodium chloride | 7.5 mg | — | 3.0 mg |
| Sodium citrate | — | 7.5 mg | 4.5 mg |
| Citric acid | 7.5 mg | 7.5 mg | 7.5 mg |
| Polysorbate 80 | 7.5 mg | 7.5 mg | 7.5 mg |
| Totally | 260.0 mg | 260 mg | 260 mg |

Preparation of coated granules:

The above core granules are coated with the same coating dispersion as used in the above Examples 3 to 4 in the same manner to give the following coated granules.

EXAMPLE 9

The core granules prepared by the formula of Example 9 as shown in Table 4 are coated with the same coating dispersion as used in the above Examples 3 to 4 under the same coating conditions as above until the weight of HPMCAS becomes 30% by weight based on the weight of the core granules to give the coated granules.

EXAMPLE 10

The core granules prepared by the formula of Example 10 as shown in Table 4 are coated with the same coating dispersion as used in the above Examples 3 to 4 under the same coating conditions as above until the weight of HPMCAS becomes 30% by weight based on the weight of the core granules to give the coated granules.

EXAMPLE 11

The core granules prepared by the formula of Example 11 as shown in Table 4 are coated with the same coating dispersion as used in the above Examples 3 to 4 under the same coating conditions as above until the weight of HPMCAS becomes 30% by weight based on the weight of the core granules to give the coated granules.

REFERENCE EXAMPLE 3

The coated granules prepared in Example 9 (equivalent to 150 mg of cilostasol) and immediate release tablets containing 50 mg of cilostazol are filled in a capsule to give a sustained release capsule (cilostazol content: 200 mg).

EXAMPLE 12 AND COMPARATIVE EXAMPLE 3

Preparation of coating dispersion:

A coating dispersion soluble in the lower digestive tract is prepared with the formula as shown in the following Table 5 in the same manner as described in Examples 1 and 2.

TABLE 5

| Material | Example 12 | Comp. Ex. 3 |
|---|---|---|
| Hydroxypropyl methylcellulose acetate succinate | 200.0 g | 200.0 g |
| Triethyl citrate | 80.0 g | 80.0 g |
| Talc | 100.0 g | 100.0 g |
| sodium laurylsulfate | 6.0 g | 6.0 g |
| Citric acid | 6.5 g | — |
| Purified water | 2607.5 g | 2614.0 g |
| Total of coating liquid | 3000.0 g | 3000.0 g |

EXAMPLE 12

The core granules prepared by the formula of Example 10 as shown in Table 4 are coated with the same coating dispersion as used in Example 12 as shown in the above Table 5 under the same coating conditions as in Examples 3 to 8 until the weight of HPMCAS becomes 32.5% by weight based on the weight of the core granules to give the coated granules.

COMPARATIVE EXAMPLE 3

The core granules prepared by the formula of Example 10 as shown in Table 4 are coated with the same coating dispersion as used in Comparative Example 3 as shown in the above Table 5 under the same coating conditions as in Examples 3 to 8 until the weight of HPMCAS becomes 32.5% by weight based on the weight of the core granules to give the coated granules.

Experiment 1

900 ml each of 1% aqueous solutions of polysorbate 80 of which pHs were adjusted to 6.5 and 7.0 by sodium dihydrogen phosphate and disodium hydrogen phosphate respectively were used as a dissolution solvent. The coated granules obtained in Examples 3 to 8 and in Comparative Examples 1 to 2 (equivalent to 15 mg of cilostazol) were subjected to the dissolution test at 75 rpm by Paddle method as defined in Japanese Pharmacopeia. The time of dissolution of 5% of medicament was deemed to be lag time. The results are shown in Table 6. The added amount of an acid (citric acid) to HPMCAS and the coating amount of HPMCAS to the core granule for coating are also shown in said Table.

TABLE 6

|  | Amount of citric acid to HPMCAS (% by weight) | Coating amount of HPMCAS to core granule (% by weight) | Lag time (minute) | |
|---|---|---|---|---|
|  |  |  | Dissolution solvent ph 6.5 | Dissolution solvent pH 7.0 |
| Comp. Ex. 1 | 0 | 53 | 45 | 22 |
| Comp. Ex. 2 |  | 75 | 66 | 31 |
| Example 3 | 1 | 40 | 241 | 50 |
| Example 4 |  | 60 | 450 | 94 |
| Example 5 | 3 | 40 | 302 | 63 |
| Example 6 |  | 60 | 563 | 113 |
| Example 7 | 5 | 40 | 350 | 75 |
| Example 8 |  | 60 | 601 | 130 |

As is shown in the above Table 6, the lag time was remarkably extended in both solutions of pH 6.5 and pH 7.0 in every Example. This indicates that the medicament was sufficiently dissolved out in the pH range of from the small intestine to the large intestine, and hence, it is assumed that desired effects of sustained release of the medicament for a long time would be achieved. On the contrary, the coated granules of Comparative Examples wherein no acid was added showed inferior lag time, and hence, it is assumed that those did not show the desired sustained release effects.

Besides, the results of dissolution test with the dissolution solvent of pH 6.5 are shown in the accompanying FIG. 1. As shown in FIG. 1, in the preparations of Comparative Examples 1 to 2, the medicament was almost dissolved out within a short time, but on the other hand, in the preparations of Examples 3 to 8, the medicament was smoothly dissolved out after a lag time of several hours, from which it is considered that the preparations can release sufficiently after reaching to the large intestine.

In the preparation soluble in the lower digestive tract of the present invention, the coating film has improved alkali resistance by the addition of an acid to the HPMCAS coating base material which dissolves at around pH 7. The preparation having such a coating film shows an alkali resistance up to about pH 7.0 which is deemed to be similar to that in the small intestine region and thereby the preparation can reach to the large intestine at the lower digestive tract, and after reaching to the large intestine, the coating film dissolves and the preparation can still release sufficient amount of the medicament.

Experiment 2

0.3% aqueous solution of sodium laurylsulfate (720 ml) which was adjusted to pH 6.5 by a citrate buffer was used as a dissolution solvent. The coated granules obtained in Example 12 and in Comparative Example 3 (which contained 80 mg of cilostazol) were subjected to the dissolution test at 50 rpm by Paddle method as defined in Japanese Pharmacopeia (=Paddle method). In addition, another dissolution test was done by using a dissolution solvent which was further incorporated with polyacetal beads (diameter: 5 mm) (about 2000 pieces) so that the mechanical stirring force would be increased like in the digestive tract when the preparation would be administered after meal (=Beads method). The dissolution profile of the coated granules of Example 12 and Comparative Example 3 are shown in the accompanying FIG. 2. Further, the time of dissolution of 5% of Medicament as a lag time is also shown in Table 7.

TABLE 7

|  | Test method | 5% dissolution time |
| --- | --- | --- |
| Example 12 | Paddle method | 312 minutes |
|  | Beads method | 185 minutes |
| Comparative Example 3 | Paddle method | 65 minutes |
|  | Beads method | 50 minutes |

As is shown in Table 7, the coated granules of Example 12 of the present invention showed much remarkably extended lag time in comparison with the coated granules of Comparative Example 3, and as shown in FIG. 2, in the preparations of Comparative Example 3, the medicament was almost dissolved out within a short period, but on the other hand, in the preparations of Example 12 of the present invention, the medicament was smoothly dissolved out after a lag time of several hours, from which it is considered that the preparation can release sufficiently after reaching to the large intestine.

INDUSTRIAL APPLICABILITY

According to the present invention using a coating dispersion prepared by incorporating a plasticizer, an anion surfactant and a prescribed amount of an acid in an aqueous dispersion of a predetermined concentration of HPMCAS which has an average particle size of 10 μm or less and dissolves at around pH 7, the preparation such as granules coated by the dispersion can reach to the large intestine at the lower digestive tract without dissolving in the small intestine when orally administered, and after reaching to the large intestine, the coating film is dissolved and then the granules release the medicament. Accordingly, the preparation of the present invention is suitable for the pharmaceutical composition which can release the active medicament continuously for a long period, particularly for a pharmaceutical preparation which can keep a sufficiently high level of blood concentration of the medicament for 24 hours even by administration once a day.

The invention claimed is:

1. A coating dispersion soluble in the lower digestive tract comprising a hydroxypropyl methylcellulose acetate succinate soluble at around pH 7, an acid, a plasticizer and an anion surfactant, wherein the hydroxypropyl methylcellulose acetate succinate has an average particle size of 10 μm or less which is dispersed at a concentration of from 2 to 20% by weight in water, and the acid is present in an amount of from 1 to 10 parts by weight per 100 parts by weight of the hydroxypropyl methylcellulose acetate succinate.

2. The coating dispersion soluble in the lower digestive tract according to claim 1, wherein the acid is one or more of the members selected from the group consisting of citric acid, ascorbic acid, adipic acid, ethylenediaminetetraacetic acid, lactic acid, succinic acid, phosphoric acid, a high molecular acid, and an acidic ion exchange resin.

3. The coating dispersion soluble in the lower digestive tract according to claim 2, wherein the plasticizer is triethyl citrate, triacetin or both, and the anion surfactant is one or more of the members selected from the group consisting of sodium alkylsulfate, fatty acid sodium salt, and fatty acid potassium salt.

4. The coating dispersion soluble in the lower digestive tract according to claim 3, wherein the acid is one or more of the members selected from the group consisting of citric acid, ascorbic acid, adipic acid, ethylenediaminetetraacetic acid, lactic acid, succinic acid.

5. The coating dispersion soluble in the lower digestive tract according to claim 3, wherein the acid is contained in an amount of from 2 to 5 parts by weight per 100 parts by weight of the hydroxypropyl methylcellulose acetate succinate.

6. The coating dispersion soluble in the lower digestive tract according to claim 4, which comprises a hydroxypropyl methylcellulose acetate succinate, citric acid, triethyl citrate, and sodium laurylsulfate.

7. A coated granule for delivery to the large intestine, which comprises a medicament-containing granular core which is coated with the coating dispersion soluble in the lower digestive tract according to any one of claims 1 to 6.

8. The coated granule for delivery to the large intestine according to claim 7, wherein the medicament is cilostazol.

* * * * *